US012754177B2

(12) United States Patent
Yang et al.

(10) Patent No.: US 12,754,177 B2
(45) Date of Patent: Oct. 6, 2026

(54) SYSTEM FOR NOTIFYING ENVIRONMENTAL POLLUTION STATUS

(71) Applicant: FAR EASTONE TELECOMMUNICATIONS CO., LTD., Taipei City (TW)

(72) Inventors: Chia-Jui Yang, Taipei City (TW); Herman Chunghwa Rao, Taipei City (TW); Chun-Chieh Kuo, Taipei City (TW); Hua-Pei Chiang, Taipei City (TW); Shui-Shu Hsiao, Taipei City (TW); Zheng-Xiang Chang, Taipei City (TW); Chyi-Dar Jang, Taipei City (TW); Tsung-Jen Wang, Taipei City (TW); Che-Yu Liao, Taipei City (TW); Chih-Min Chan, Taipei City (TW); Teng-Chieh Yang, Taipei City (TW); Chang-Hung Hsu, Taipei City (TW)

(73) Assignee: FAR EASTONE TELECOMMUNICATIONS CO., LTD., Taipei City (TW)

( * ) Notice: Subject to any disclaimer, the term of this patent is extended or adjusted under 35 U.S.C. 154(b) by 123 days.

(21) Appl. No.: 18/772,905

(22) Filed: Jul. 15, 2024

(65) Prior Publication Data

US 2025/0044270 A1 Feb. 6, 2025

Related U.S. Application Data

(60) Provisional application No. 63/585,277, filed on Sep. 26, 2023, provisional application No. 63/530,110, filed on Aug. 1, 2023.

(51) Int. Cl.

| | |
|---|---|
| ***G01N 33/00*** | (2006.01) |
| ***G06T 7/00*** | (2017.01) |

(52) U.S. Cl.

CPC ....... *G01N 33/0075* (2013.01); *G06T 7/0012* (2013.01); *G06T 2207/10048* (2013.01); *G06T 2207/30201* (2013.01)

(58) Field of Classification Search

CPC ........... G01N 33/0075; G01N 33/0036; G01N 33/0067; G01N 33/006; G08B 21/14; G08B 21/182; G08B 23/00

See application file for complete search history.

(56) References Cited

U.S. PATENT DOCUMENTS 11,906,415 B1 * 2/2024 Galburt .............. G01N 15/1459
2012/0297028 A1 * 11/2012 Das ........................ G01D 21/02 709/217

(Continued)

*Primary Examiner* — Mirza F Alam
(74) *Attorney, Agent, or Firm* — MUNCY, GEISSLER, OLDS & LOWE, P.C.

(57) ABSTRACT

A system for notifying environmental pollution status includes wireless environment sensing devices and a portable wireless environmental pollution status notification device. The wireless environment sensing devices, respectively arranged in the different sensing locations of a physical environment, respectively store the sensing locations and respectively sense pollution related information corresponding to the different sensing locations to output the pollution related information and the sensing locations corresponding thereto. The portable wireless environmental pollution status notification device, wirelessly connected to the plurality of wireless environment sensing devices and located in the physical environment, receives the pollution related information and the sensing locations corresponding thereto and generates notification signals based on the pollution related information and the sensing locations corresponding thereto.

30 Claims, 6 Drawing Sheets

(56) References Cited

U.S. PATENT DOCUMENTS

| | | | | |
|---|---|---|---|---|
| 2013/0144527 A1* | 6/2013 | Kuhnreichi | G01N 33/00 | |
| | | | 702/2 | |
| 2015/0052975 A1* | 2/2015 | Martin | F24F 11/62 | |
| | | | 73/31.02 | |
| 2017/0353777 A1* | 12/2017 | Mach | G08B 21/12 | |

* cited by examiner

Fig. 6
112
BA
concentration of Escherichia coli
1900CFU/m³ (Exceeding the
standard)

SYSTEM FOR NOTIFYING ENVIRONMENTAL POLLUTION STATUS

This application claims priority for the U.S. provisional patent application Nos. 63/530,110 filed on 1 Aug. 2023, and 63/585,277 filed on 26 Sep. 2023, the contents of which are incorporated by reference in their entirety.

BACKGROUND OF THE INVENTION

Field of the Invention

The present invention relates to a notification system, particularly to a system for notifying environmental pollution status.

Description of the Related Art

With the advancement of industry and commerce, modern people spend more and more time indoors. Most of the buildings in recent years have closed designs. Often due to poor ventilation in the indoor environment, air pollutants are easy to accumulate in the indoor environment, which affects human health. Compared with the outdoor environment, the concentration of indoor air pollutants is often higher than that of outdoor air pollutants. Therefore, the importance and safety of indoor air quality are more concerned and valued by people.

Generally, there are many sources of pollutants that cause indoor air pollution, such as cooking, smoking, spraying, or human activities of using indoor building materials, plywood, and resin adhesives, which may produce hazardous pollutants such as volatile organic compounds and suspended particles. Therefore, in addition to increasing the ventilation rate of the indoor environment, air purifiers can also be used to effectively remove indoor air pollutants in order to improve indoor air quality. However, air purifiers can only remove parts of the pollutants in the indoor space. No one knows which part of the indoor space has more pollutants and which part of the indoor space has fewer pollutants.

To overcome the abovementioned problems, the present invention provides a system for notifying environmental pollution status, so as to solve the afore-mentioned problems of the prior art.

SUMMARY OF THE INVENTION

The present invention provides a system for notifying environmental pollution status, which implements environmental detection distribution in three-dimensional space to provide a recommended path.

In an embodiment of the present invention, a system for notifying environmental pollution status includes a plurality of wireless environment sensing devices and a portable wireless environmental pollution status notification device. The wireless environment sensing devices are respectively arranged in different sensing locations of a physical environment and configured to respectively store the sensing locations and respectively sense pollution related information corresponding to the different sensing locations to output the pollution related information and the sensing locations corresponding thereto. The portable wireless environmental pollution status notification device is wirelessly connected to the plurality of wireless environment sensing devices, located in the physical environment, and configured to receive the pollution related information and the sensing locations corresponding thereto and generate notification signals based on the pollution related information and the sensing locations corresponding thereto.

In an embodiment of the present invention, the plurality of wireless environment sensing devices are wirelessly connected to the portable wireless environmental pollution status notification device using WiFi direct technology and Bluetooth® technology.

In an embodiment of the present invention, each of the plurality of wireless environment sensing devices includes at least one first pollutant sensor, a first image sensor, a first thermal imaging camera, a storage device, a first wireless communication module, and a first processor. The first pollutant sensor is configured to measure the first pollution parameter of first pollutants corresponding to the sensing location. The first image sensor and the first thermal imaging camera are configured to respectively capture a first visible light image and a first thermal image within the same range. The storage device is configured to store the sensing location. The first wireless communication module is wirelessly connected to the portable wireless environmental pollution status notification device. The first processor is electrically connected to the at least one first pollutant sensor, the first image sensor, the first thermal imaging camera, the storage device, and the first wireless communication module and configured to extract a first temperature range of the first thermal image, use the first pollution parameter as the pollution related information, and transmit the sensing location and the first pollution parameter to the portable wireless environmental pollution status notification device through the first wireless communication module.

In an embodiment of the present invention, the first pollution parameter is a pollution concentration, a wind speed, a pollution range, or a flame burning intensity.

In an embodiment of the present invention, when the first pollution parameter is greater than a given value, the first processor notifies the portable wireless environmental pollution status notification device through the first wireless communication module that the sensing location corresponding to the first pollution parameter greater than the given value is a polluted location.

In an embodiment of the present invention, when the first visible light image has a human face image and the first temperature range is greater than a given temperature for a given time period, the first processor notifies the portable wireless environmental pollution status notification device through the first wireless communication module that the sensing location corresponding to the first temperature range greater than the given temperature is a polluted location.

In an embodiment of the present invention, when the first visible light image has a human face image and the first temperature range is greater than a given temperature for a given time period, the first processor transmits the human face image to the portable wireless environmental pollution status notification device through the first wireless communication module.

In an embodiment of the present invention, when the first visible light image has a human face image and the first pollution parameter is greater than a given value for a given time period, the first processor transmits the human face image to the portable wireless environmental pollution status notification device through the first wireless communication module.

In an embodiment of the present invention, the first pollutant sensor is an optical finger navigation (OFN) sensor.

In an embodiment of the present invention, the first pollutants include bacteria, mold, viruses, flame, smoke, liquefied gas, carbon monoxide, carbon dioxide, ozone, alkane gases, benzene gases, ketone gases, natural gas, coal gas, gasoline, chlorine, ammonia, flammable gases, harmful volatile matter, or airborne matter.

In an embodiment of the present invention, the notification signals include an image signal, a sound signal, and a vibration signal. The portable wireless environmental pollution status notification device includes a second wireless communication module, a second processor, a portable display, at least one portable sound player, and a portable vibrator. The second wireless communication module is wirelessly connected to the first wireless communication module. The second processor is electrically connected to the second wireless communication module and configured to receive the sensing location and the first pollution parameter through the second wireless communication module. The portable display is electrically connected to the second processor. The second processor is configured to drive the portable display to generate the image signal based on a given condition, the sensing location, and the first pollution parameter. The portable sound player is electrically connected to the second processor. The second processor is configured to drive the at least one portable sound player to generate the sound signal based on the sensing location and the first pollution parameter. The portable vibrator is electrically connected to the second processor. The second processor is configured to drive the portable vibrator to generate the vibration signal based on the sensing location and the first pollution parameter.

In an embodiment of the present invention, the at least one portable sound player includes a plurality of portable sound players.

In an embodiment of the present invention, the given condition includes one of the different sensing locations as an ending location. The second processor is configured to receive reference signal received power (RSRP), signal-to-interference-plus-noise ratios (SINRs), packet round-trip time (RTT), angles of arrival, and angles of departure from the first wireless communication module through the second wireless communication module and calculate a starting location based on at least three of the different sensing locations and the RSRP, the SINRs, the packet RTT, the angles of arrival, and the angles of departure corresponding thereto. The second processor is configured to plan candidate paths connected between the ending location and the starting location based on the different sensing locations, calculate risk values corresponding to the candidate paths, and select the candidate path corresponding to the highest one or the lowest one of the risk values as a recommended path.

$$\text{The risk value} = \sum_{i=1}^{n} \frac{Pi}{Di}.$$

Di represents a distance between the starting location and the i-th sensing location corresponding to the candidate path. Pi represents the first pollution parameter measured in the i-th sensing location corresponding to the candidate path. n represents the total number of the sensing locations corresponding to the candidate path. The image signal shows the recommended path and an image corresponding to the sensing locations, the first pollutants, and the first pollution parameter.

In an embodiment of the present invention, the portable wireless environmental pollution status notification device further includes at least one second pollutant sensor, a second image sensor, and a second thermal imaging camera. The second pollutant sensor is electrically connected to the second processor and configured to measure a second pollution parameter of second pollutants corresponding to the starting location. The second pollutants and the first pollutants belong to identical pollutants and the second pollution parameter and the first pollution parameter belong to identical pollution parameters. The second image sensor and the second thermal imaging camera are electrically connected to the second processor and configured to respectively capture a second visible light image and a second thermal image within the same range corresponding to the starting location. The second processor is configured to obtain the second temperature range of the second thermal image. When the sensing location is the starting location, the second processor respectively uses the second pollution parameter and the second temperature range to replace the corresponding first pollution parameter and the corresponding first temperature range.

In an embodiment of the present invention, when the second pollution parameter is greater than a given value, the second processor drives the portable display to display that the sensing location corresponding to the second pollution parameter greater than the given value is a polluted location.

In an embodiment of the present invention, when the second visible light image has a human face image and the second temperature range is greater than a given temperature for a given time period, the second processor drives the portable display to display the sensing position corresponding to the second temperature greater than the given temperature is a polluted location.

In an embodiment of the present invention, when the second visible light image has a human face image and the second temperature range is greater than a given temperature, the second processor drives the portable display to display the human face image as a source of infection.

In an embodiment of the present invention, when the second visible light image has a human face image and the second pollution parameter is greater than a given value for a given time period, the second processor drives the portable display to display the human face image as a source of infection.

In an embodiment of the present invention, the system for notifying environmental pollution status further includes at least one wireless base station and a cloud server. The wireless base station is wirelessly connected to the plurality of wireless environment sensing devices and the portable wireless environmental pollution status notification device. The cloud server is electrically connected to the wireless base station. The plurality of wireless environment sensing devices are configured to transmit the pollution related information and the sensing locations corresponding thereto to the cloud server through the wireless base station. The cloud server is configured to transmit the pollution related information and the sensing locations corresponding thereto to the portable wireless environmental pollution status notification device through the wireless base station.

In an embodiment of the present invention, the wireless base station is a 3G base station, a 4G base station, a 5G base station, a Bluetooth® base station, or a WiFi base station.

In an embodiment of the present invention, each of the plurality of wireless environment sensing devices includes at least one first pollutant sensor, a first image sensor, a first thermal imaging camera, a storage device, a first wireless communication module, and a first processor. The first pollutant sensor is configured to measure the first pollution parameter of first pollutants corresponding to the sensing location. The first image sensor and the first thermal imaging camera are configured to respectively capture a first visible light image and a first thermal image within the same range. The storage device is configured to store the sensing location. The first wireless communication module is wirelessly connected to the wireless base station. The first processor is electrically connected to the first pollutant sensor, the first image sensor, the first thermal imaging camera, the storage device, and the first wireless communication module and configured to extract the first temperature range of the first thermal image, use the first pollution parameter as the pollution related information, and transmit the sensing location and the first pollution parameter to the cloud server through the first wireless communication module and the wireless base station.

In an embodiment of the present invention, the first pollution parameter is a pollution concentration, a wind speed, a pollution range, or a flame burning intensity.

In an embodiment of the present invention, when the first pollution parameter is greater than a given value, the first processor notifies the portable wireless environmental pollution status notification device through the first wireless communication module, the wireless base station, and the cloud server that the sensing location corresponding to the first pollution parameter greater than the given value is a polluted location.

In an embodiment of the present invention, when the first visible light image has a human face image and the first temperature range is greater than a given temperature for a given time period, the first processor notifies the portable wireless environmental pollution status notification device through the first wireless communication module, the wireless base station, and the cloud server that the sensing location corresponding to the first temperature range greater than the given temperature is a polluted location.

In an embodiment of the present invention, when the first visible light image has a human face image and the first temperature range is greater than a given temperature for a given time period, the first processor transmits the human face image to the portable wireless environmental pollution status notification device through the first wireless communication module, the wireless base station, and the cloud server.

In an embodiment of the present invention, when the first visible light image has a human face image and the first pollution parameter is greater than a given value for a given time period, the first processor transmits the human face image to the portable wireless environmental pollution status notification device through the first wireless communication module, the wireless base station, and the cloud server.

In an embodiment of the present invention, the first pollutant sensor is an optical finger navigation (OFN) sensor.

In an embodiment of the present invention, the first pollutants include bacteria, mold, viruses, flame, smoke, liquefied gas, carbon monoxide, carbon dioxide, ozone, alkane gases, benzene gases, ketone gases, natural gas, coal gas, gasoline, chlorine, ammonia, flammable gases, harmful volatile matter, or airborne matter.

In an embodiment of the present invention, the notification signals include an image signal, a sound signal, and a vibration signal. The portable wireless environmental pollution status notification device includes a second wireless communication module, a second processor, a portable display, at least one portable sound player, and a portable vibrator. The second wireless communication module is wirelessly connected to the wireless base station. The second processor is electrically connected to the second wireless communication module and configured to receive the sensing location and the first pollution parameter through the second wireless communication module. The portable display is electrically connected to the second processor. The second processor is configured to drive the portable display to generate the image signal based on a given condition, the sensing location, and the first pollution parameter. The portable sound player is electrically connected to the second processor. The second processor is configured to drive the portable sound player to generate the sound signal based on the sensing location and the first pollution parameter. The portable vibrator is electrically connected to the second processor. The second processor is configured to drive the portable vibrator to generate the vibration signal based on the sensing location and the first pollution parameter.

In an embodiment of the present invention, the at least one portable sound player includes a plurality of portable sound players.

In an embodiment of the present invention, the given condition includes one of the different sensing locations as an ending location. The second processor is configured to receive reference signal received power (RSRP), signal-to-interference-plus-noise ratios (SINRs), packet round-trip time (RTT), angles of arrival, angles of departure, and the location of the wireless base station from the wireless base station through the second wireless communication module and calculate a starting location based on the RSRP, the SINRs, the packet RTT, the angles of arrival, the angles of departure, and the location of the wireless base station. The second processor is configured to plan candidate paths connected between the ending location and the starting location based on the different sensing locations, calculate risk values corresponding to the candidate paths, and select the candidate path corresponding to the highest one or the lowest one of the risk values as a recommended path.

$$\text{The risk value} = \sum_{i=1}^{n} \frac{Pi}{Di},$$

Di represents a distance between the starting location and the i-th sensing location corresponding to the candidate path. Pi represents the first pollution parameter measured in the i-th sensing location corresponding to the candidate path. n represents the total number of the sensing locations corresponding to the candidate path. The image signal shows the recommended path and an image corresponding to the sensing locations, the first pollutants, and the first pollution parameter.

In an embodiment of the present invention, the portable wireless environmental pollution status notification device further includes at least one second pollutant sensor, a second image sensor and a second thermal imaging camera. The second pollutant sensor is electrically connected to the second processor and configured to measure the second pollution parameter of second pollutants corresponding to the starting location. The second pollutants and the first pollutants belong to identical pollutants and the second pollution parameter and the first pollution parameter belong to identical pollution parameters. The second image sensor and the second thermal imaging camera are electrically connected to the second processor and configured to respectively capture a second visible light image and a second thermal image within the same range corresponding to the starting location. The second processor is configured to obtain the second temperature range of the second thermal image. When the sensing location is the starting location, the second processor respectively uses the second pollution parameter and the second temperature range to replace the corresponding first pollution parameter and the corresponding first temperature range.

In an embodiment of the present invention, when the second pollution parameter is greater than a given value, the second processor drives the portable display to display that the sensing location corresponding to the second pollution parameter greater than the given value is a polluted location.

In an embodiment of the present invention, when the second visible light image has a human face image and the second temperature range is greater than a given temperature for a given time period, the second processor drives the portable display to display the sensing position corresponding to the second temperature greater than the given temperature is a polluted location.

In an embodiment of the present invention, when the second visible light image has a human face image and the second temperature range is greater than a given temperature, the second processor drives the portable display to display the human face image as a source of infection.

In an embodiment of the present invention, when the second visible light image has a human face image and the second pollution parameter is greater than a given value for a given time period, the second processor drives the portable display to display the human face image as a source of infection.

To sum up, the system for notifying environmental pollution status uses the wireless environment sensing devices to implement environmental detection distribution in three-dimensional space, thereby providing a recommended path.

Below, the embodiments are described in detail in cooperation with the drawings to make easily understood the technical contents, characteristics and accomplishments of the present invention.

DETAILED DESCRIPTION OF THE INVENTION

Figure 1:
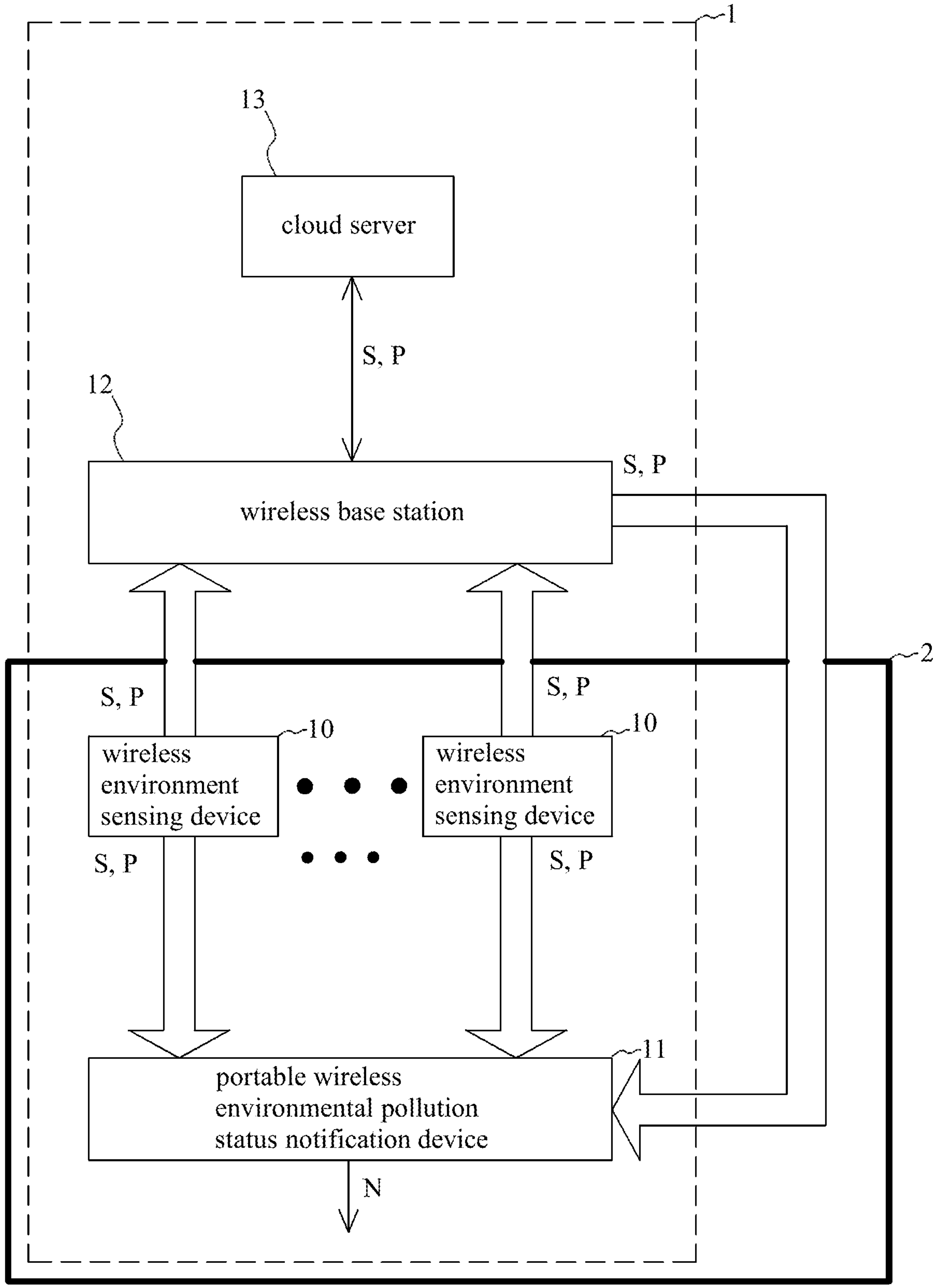
FIG. 1 is a schematic diagram illustrating a system for notifying environmental pollution status according to an embodiment of the present invention.

Reference will now be made in detail to embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, methods and apparatus in accordance with the present disclosure. It is to be understood that elements not specifically shown or described may take various forms well known to those skilled in the art. Many alternatives and modifications will be apparent to those skilled in the art, once informed by the present disclosure.

When an element is referred to as being “on” another element, it can be directly on the other element or intervening elements may be present therebetween. In contrast, when an element is referred to as being “directly on” another element, there are no intervening elements present. As used herein, the term “and/or” includes any and all combinations of one or more of the associated listed items.

Reference throughout this specification to “one embodiment” or “an embodiment” means that a particular feature, structure, or characteristic described in connection with the embodiment is included in at least one embodiment. Thus, the appearances of the phrases “in one embodiment” or “in an embodiment” in various places throughout this specification are not necessarily all referring to the same embodiment.

The invention is particularly described with the following examples which are only for instance. Those skilled in the art will readily observe that numerous modifications and alterations of the device and method may be made while retaining the teachings of the invention. Accordingly, the following disclosure should be construed as limited only by the metes and bounds of the appended claims. In the whole patent application and the claims, except for clearly described content, the meaning of the articles “a” and “the” includes the meaning of “one or at least one” of the elements or components. Moreover, in the whole patent application and the claims, except that the plurality can be excluded obviously according to the context, the singular articles also contain the description for the plurality of elements or components. In the entire specification and claims, unless the contents clearly specify the meaning of some terms, the meaning of the article “wherein” includes the meaning of the articles “wherein” and “whereon”. The meanings of every term used in the present claims and specification refer to a usual meaning known to one skilled in the art unless the meaning is additionally annotated. Some terms used to describe the invention will be discussed to guide practitioners about the invention. The examples in the present specification do not limit the claimed scope of the invention.

Furthermore, it can be understood that the terms “comprising,” “including,” “having,” “containing,” and “involving” are open-ended terms, which refer to “may include but is not limited to so.” In addition, each of the embodiments or claims of the present invention is not necessary to achieve all the effects and advantages possibly to be generated, and the abstract and title of the present invention is used to assist for patent search and is not used to further limit the claimed scope of the present invention.

Further, in the present specification and claims, the term “comprising” is open type and should not be viewed as the term “consisted of.” In addition, the term “electrically coupled” can be referring to either directly connecting or indirectly connecting between elements. Thus, if it is described in the below contents of the present invention that a first device is electrically coupled to a second device, the first device can be directly connected to the second device, or indirectly connected to the second device through other devices or means. Moreover, when the transmissions or generations of electrical signals are mentioned, one skilled in the art should understand some degradations or undesirable transformations could be generated during the operations. If it is not specified in the specification, an electrical signal at the transmitting end should be viewed as substantially the same signal as that at the receiving end. For example, when the end A of an electrical circuit provides an electrical signal S to the end B of the electrical circuit, the voltage of the electrical signal S may drop due to passing through the source and drain of a transistor or due to some parasitic capacitance. However, the transistor is not deliberately used to generate the effect of degrading the signal to achieve some result, that is, the signal S at the end A should be viewed as substantially the same as that at the end B.

Unless otherwise specified, some conditional sentences or words, such as “can”, “could”, “might”, or “may”, usually attempt to express what the embodiment in the present invention has, but it can also be interpreted as a feature, element, or step that may not be needed. In other embodiments, these features, elements, or steps may not be required.

In the following description, a system for notifying environmental pollution status will be provided, which uses wireless environment sensing devices to implement environmental detection distribution in three-dimensional space, thereby providing a recommended path.

FIG. 1 is a schematic diagram illustrating a system for notifying environmental pollution status according to an embodiment of the present invention. Referring to FIG. 1, a system 1 for notifying environmental pollution status is introduced as follows. The system 1 for notifying environmental pollution status includes a plurality of wireless environment sensing devices 10 and a portable wireless environmental pollution status notification device 11. The portable wireless environmental pollution status notification device 11 may be installed on a user and follows the user’s movements. The wireless environment sensing devices 10 are respectively arranged in the different sensing locations S of a physical environment 2. The portable wireless environmental pollution status notification device 11 is wirelessly connected to the wireless environment sensing devices 10 and located in the physical environment 2. For example, the wireless environment sensing devices 10 are wirelessly connected to the portable wireless environmental pollution status notification device 11 using WiFi direct technology and Bluetooth® technology. The wireless environment sensing devices 10 respectively store the sensing locations S and respectively sense pollution related information P corresponding to the different sensing locations S to output the pollution related information P and the sensing locations S corresponding thereto. The portable wireless environmental pollution status notification device 11 receives the pollution related information P and the sensing locations S corresponding thereto and generates notification signals N based on the pollution related information P and the sensing locations S corresponding thereto. The notification signals N may include an image signal, a sound signal, and a vibration signal. The sensing location S can be expressed in a rectangular coordinate system or a spherical coordinate system.

Figure 2:
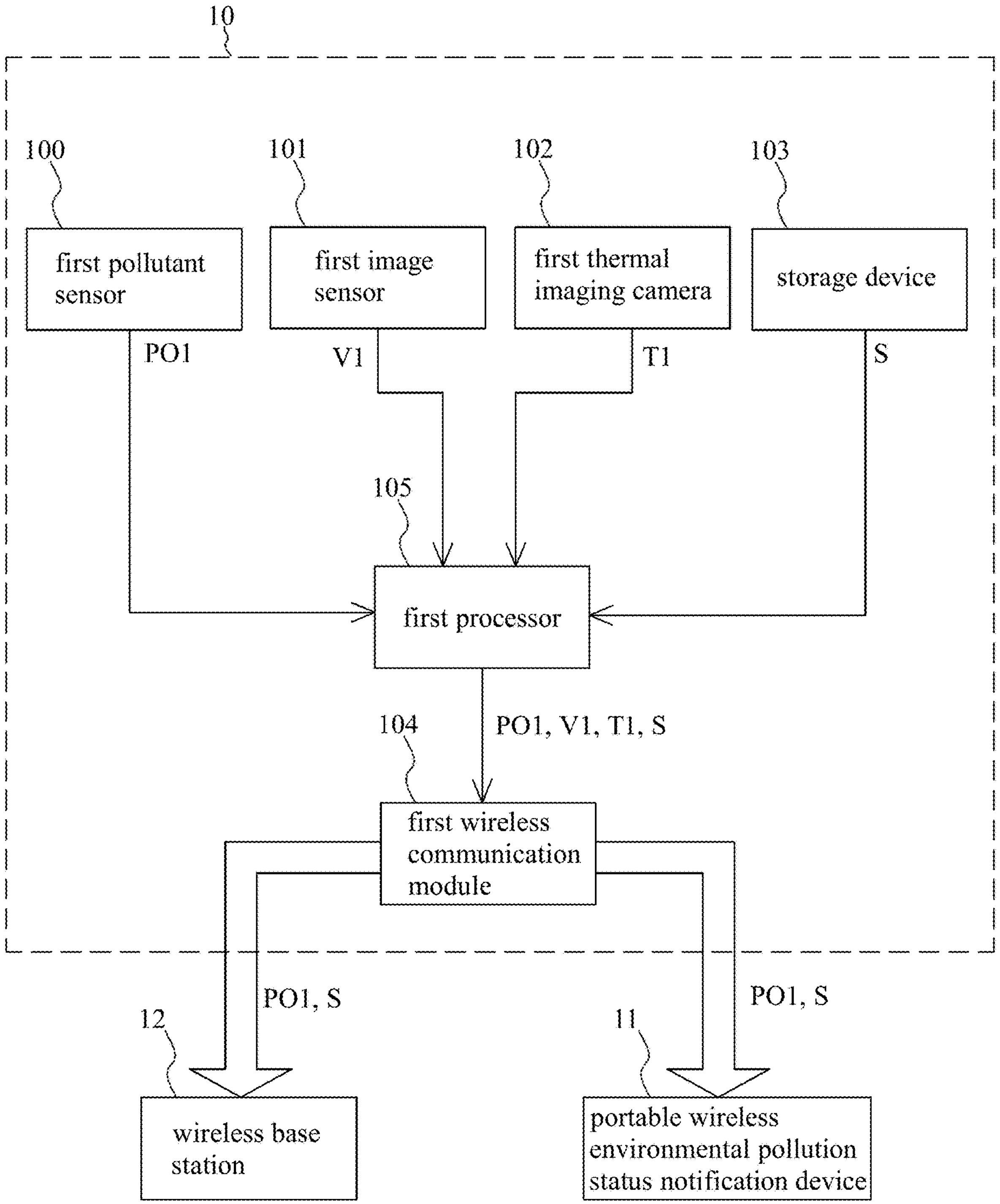
FIG. 2 is a schematic diagram illustrating a wireless environment sensing device according to an embodiment of the present invention.

FIG. 2 is a schematic diagram illustrating a wireless environment sensing device according to an embodiment of the present invention. Referring to FIG. 2, each of the wireless environment sensing devices 10 includes at least one first pollutant sensor 100, a first image sensor 101, a first thermal imaging camera 102, a storage device 103, a first wireless communication module 104, and a first processor 105. For convenience and clarity, the number of the first pollutant sensor 100 is one. The first wireless communication module 104 is wirelessly connected to the portable wireless environmental pollution status notification device 11 using WiFi direct technology and Bluetooth® technology. The first processor 105 is electrically connected to the first pollutant sensor 100, the first image sensor 101, the first thermal imaging camera 102, the storage device 103, and the first wireless communication module 104. The first pollutant sensor 100 measures the first pollution parameter PO1 of first pollutants corresponding to the sensing location S. For example, the first pollutants may include, but are not limited to, bacteria, mold, viruses, flame, smoke, liquefied gas, carbon monoxide, carbon dioxide, ozone, alkane gases, benzene gases, ketone gases, natural gas, coal gas, gasoline, chlorine, ammonia, flammable gases, harmful volatile matter, or airborne matter. The first pollutant sensor 100 may be, but not limited to, an optical finger navigation (OFN) sensor, a wind speed sensor, a chemical sensor, or an optical sensor. When the pollutant is carbon monoxide, the carbon monoxide will absorb the infrared rays with a wavelength of about 4700 nanometers generated by the OFN sensor. The carbon monoxide will reflect the infrared rays back to the OFN sensor. The difference between the intensities of the reflected and generated infrared rays is used to calculate the concentration of carbon monoxide. The first pollution parameter PO1 may be, but not limited to, a pollution concentration, a wind speed, a pollution range, or a flame burning intensity. The first image sensor 101 and the first thermal imaging camera 102 respectively capture a first visible light image V1 and a first thermal image T1 within the same range. The storage device 103 stores the sensing location S. The first processor 105 extracts the first temperature range of the first thermal image T1, uses the first pollution parameter PO1 as the pollution related information, and transmits the sensing location S and the first pollution parameter PO1 to the portable wireless environmental pollution status notification device 11 through the first wireless communication module 104.

When the first pollution parameter PO1 is greater than a given value, the first processor 105 notifies the portable wireless environmental pollution status notification device 11 through the first wireless communication module 104 that the sensing location S corresponding to the first pollution parameter PO1 greater than the given value is a polluted location. When the first visible light image V1 has a human face image and the first temperature range is greater than a given temperature for a given time period, the first processor 105 notifies the portable wireless environmental pollution status notification device 11 through the first wireless communication module 104 that the sensing location S corresponding to the first temperature range greater than the given temperature is a polluted location. When the first visible light image V1 has a human face image and the first temperature range is greater than a given temperature for a given time period, the first processor 105 transmits the human face image to the portable wireless environmental pollution status notification device 11 through the first wireless communication module 104. When the first visible light image V1 has a human face image and the first pollution parameter PO1 is greater than a given value for a given time period, the first processor 105 transmits the human face image to the portable wireless environmental pollution status notification device 11 through the first wireless communication module 104.

Figure 3:
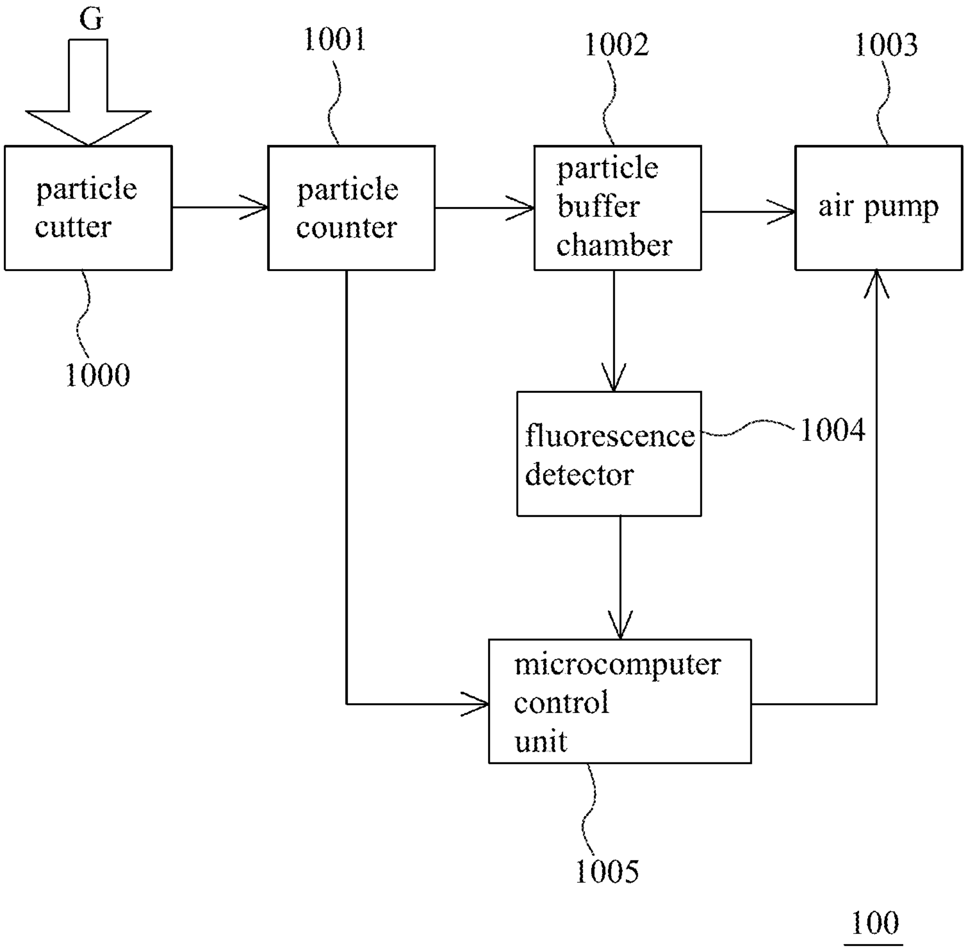
FIG. 3 is a schematic diagram illustrating a first pollutant sensor according to an embodiment of the present invention.

FIG. 3 is a schematic diagram illustrating a first pollutant sensor according to an embodiment of the present invention. Please refer to FIG. 2 and FIG. 3. When the first pollutant is a bioaerosol containing bacteria, mold, or viruses, the first pollutant sensor 100 may include a particle cutter 1000, a particle counter 1001, a particle buffer chamber 1002, an air pump 1003, a fluorescence detector 1004, and a microcomputer control unit 1005. The particle cutter 1000, the particle counter 1001, the particle buffer chamber 1002, and the air pump 1003 are connected in sequence through gas pipelines. The particle buffer chamber 1002 is connected to the fluorescence detector 1004 through a gas pipeline. The microcomputer control unit 1005 is electrically connected to the first processor 105, the particle counter 1001, and the air pump 1003. When the air pump 1003 starts to operate, the air pump 1003 absorbs a bioaerosol G and transmits it to the particle cutter 1000. The particle cutter 1000 can filter out particles, water droplets, oil droplets and smoke particles with a particle diameter greater than 10 microns (μm) in the sampled bioaerosol G to avoid interference caused by non-biological aerosols that can produce fluorescence, thereby reducing the error rate of the device. The particle counter 1001 may operate based on the light scattering principle. The particle counter 1001 is placed before the particle buffer chamber 1002 and after the particle cutter 1000 to determine the optical equivalent particle diameter and the concentration of the particles of the bioaerosol G to be measured. The fluorescence detector 1002 is used to detect the fluorescence intensity of the particle clusters of the bioaerosol G in the particle buffer chamber 1002. Specifically, the fluorescence detector 1002 includes an excitation light source and a photodetector. The photodetector is used to obtain the fluorescence intensity of the particle cluster of the bioaerosol G excited by the excitation light in the particle buffer chamber 1002, convert the fluorescence intensity into an electrical signal, and transmit the electrical signal to the microcomputer control unit 1005. The microcomputer control unit 1005 divides the fluorescence intensity by the atmospheric volume to obtain the concentration of the bioaerosol G and uses the concentration of the bioaerosol G as the concentration of pollutants. The first pollutant sensor 100 can also refer to Chinese patent with application number CN201310009382.X.

Figure 4:
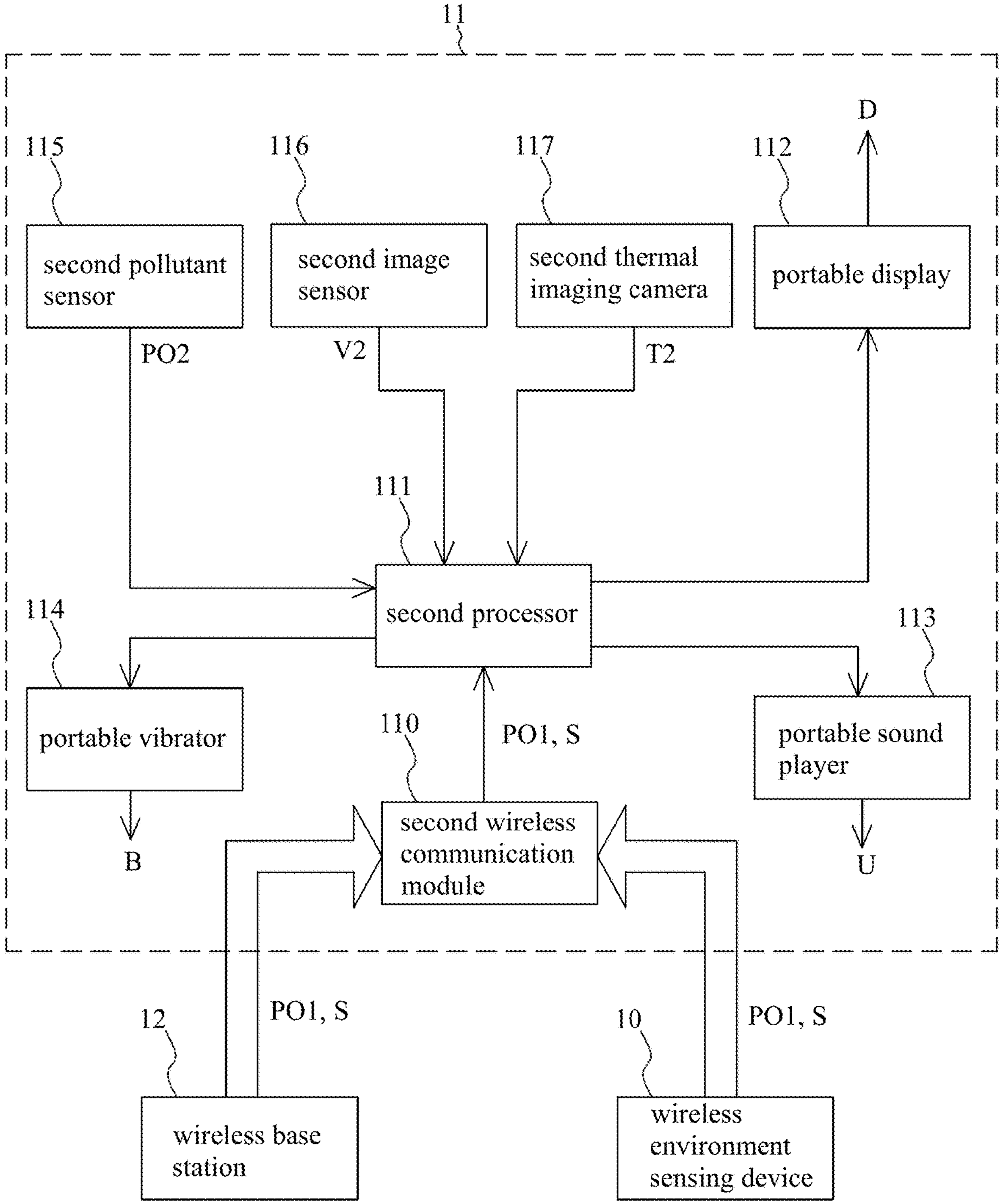
FIG. 4 is a schematic diagram illustrating a portable wireless environmental pollution status notification device according to an embodiment of the present invention.

FIG. 4 is a schematic diagram illustrating a portable wireless environmental pollution status notification device according to an embodiment of the present invention. Referring to FIG. 4 and FIG. 2, the portable wireless environmental pollution status notification device 11 may include a second wireless communication module 110, a second processor 111, a portable display 112, at least one portable sound player 113, and a portable vibrator 114. For convenience and clarity, the number of the portable sound player 113 is one. The second processor 111 is electrically connected to the second wireless communication module 110, the portable display 112, the portable sound player 113, and the portable vibrator 114. The second wireless communication module 110 is wirelessly connected to the first wireless communication module 104 using WiFi direct technology and Bluetooth® technology. The second processor 111 receives the sensing location S and the first pollution parameter PO1 through the second wireless communication module 110. The second processor 111 drives the portable display 112 to generate the image signal D based on a given condition, the sensing location S, and the first pollution parameter PO1. The second processor 111 may drive the portable display 112 to display the detected human face image or the detected polluted location and notify the user that the human face image or the polluted location is a potential source of pollution. The second processor 111 may drive the portable sound player 113 to generate the sound signal U based on the sensing location S and the first pollution parameter PO1. For example, different first pollution parameters PO1 respectively correspond to different sound signals U. If there are a plurality of portable sound players 113, the portable sound players 113 are respectively arranged on different sides of the user. The second processor 111 drives the portable vibrator 114 to generate the vibration signal B based on the sensing location S and the first pollution parameter PO1. For example, different first pollution parameters PO1 respectively correspond to different vibration frequencies or different vibration intensities of the vibration signals B.

The given condition includes one of the different sensing locations S as an ending location. The second processor 111 receives reference signal received power (RSRP), signal-to-interference-plus-noise ratios (SINRs), packet round-trip time (RTT), angles of arrival, and angles of departure from the first wireless communication module 104 through the second wireless communication module 110 and calculates the location of the second processor 111 as a starting location based on at least three of the different sensing locations S and the RSRP, the SINRs, the packet RTT, the angles of arrival, and the angles of departure corresponding thereto. The starting location is known. Thus, when the first pollution parameter PO1 corresponding to the starting location close to the sensing location S is greater, the intensity of the corresponding sound signal U or vibration signal B is greater or the vibration frequency of the corresponding vibration signal B is greater.

The second processor 111 plans candidate paths connected between the ending location and the starting location based on the different sensing locations S, calculates risk values corresponding to the candidate paths, and selects the candidate path corresponding to the highest one or the lowest one of the risk values as a recommended path.

$$\text{The risk value} = \sum_{i=1}^{n} \frac{Pi}{Di}.$$

Figure 5:
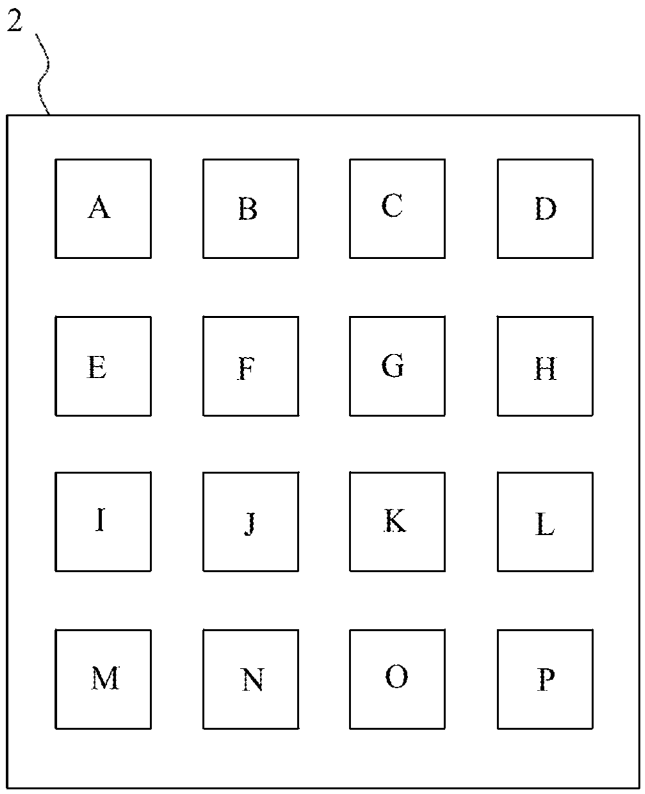
FIG. 5 is a schematic diagram illustrating sensing locations according to an embodiment of the present invention.

Di represents a distance between the starting location and the i-th sensing location corresponding to the candidate path. Pi represents the first pollution parameter PO1 measured in the i-th sensing location S corresponding to the candidate path. n represents the total number of the sensing locations S corresponding to the candidate path. The image signal D shows the recommended path and an image corresponding to the sensing locations S, the first pollutants, and the first pollution parameter PO1. FIG. 5 is a schematic diagram illustrating sensing locations according to an embodiment of the present invention. Refer to FIG. 4 and FIG. 5. Assume that the starting location is the location of area M and that the ending location is the location of area A. There are two candidate paths in total. The first candidate path includes areas I, E, and A and the second candidate path includes areas N, J, F, B, and A. Assume that coefficients Di corresponding to areas I, N, E, J, F, B and A are 1, 1, 2, 1.5, 2.5, 3.5 and 3 respectively. The first pollution parameters PO1 corresponding to areas I, N, E, J, F, B and A are respectively 5, 1, 2, 3, 8, 1 and 6. Therefore, the risk value of the first candidate path=1/1+2/2+6/3=4. The risk value of the second candidate path=1/1+3/1.5+8/2.5+1/3.5+6/3=8.2+2/7. In other words, the risk value of the second candidate path is greater than the risk value of the first candidate path. If one intends to avoid pollution sources, the first candidate path is selected as the recommended path. If one intends to clean up the pollution source, the second candidate path is selected as the recommended path.

Referring to FIG. 4, the portable wireless environmental pollution status notification device 11 may further include at least one second pollutant sensor 115, a second image sensor 116, and a second thermal imaging camera 117. For convenience and clarity, the number of the second pollutant sensor 115 is one. The second pollutant sensor 115, the second image sensor 116, and the second thermal imaging camera 117 are electrically connected to the second processor 111. The second pollutant sensor 115 measures the second pollution parameter PO2 of second pollutants corresponding to the starting location. The second pollutant sensor 115 and the first pollutant sensor are identical pollutant sensors. The second pollutants and the first pollutants belong to identical pollutants and the second pollution parameter PO2 and the first pollution parameter PO1 belong to identical pollution parameters. The second image sensor 116 and the second thermal imaging camera 117 respectively capture a second visible light image V2 and a second thermal image T2 within the same range corresponding to the starting location. The second processor 111 obtains the second temperature range of the second thermal image T2. When the sensing location S is the starting location, the second processor 111 respectively uses the second pollution parameter PO2 and the second temperature range to replace the corresponding first pollution parameter PO1 and the corresponding first temperature range.

When the second pollution parameter PO2 is greater than a given value, the second processor 111 drives the portable display 112 to display that the sensing location S corresponding to the second pollution parameter PO2 greater than the given value is a polluted location. When the second visible light image V2 has a human face image and the second temperature range is greater than a given temperature for a given time period, the second processor 111 drives the portable display 112 to display the sensing position S corresponding to the second temperature greater than the given temperature is a polluted location. When the second visible light image V2 has a human face image and the second temperature range is greater than a given temperature, the second processor 111 drives the portable display 112 to display the human face image as a source of infection. When the second visible light image V2 has a human face image and the second pollution parameter PO2 is greater than a given value for a given time period, the second processor 111 drives the portable display 112 to display the human face image as a source of infection.

Figure 6:
FIG. 6 is a schematic diagram illustrating an image displayed by a portable display according to an embodiment of the present invention.

FIG. 6 is a schematic diagram illustrating an image displayed by a portable display according to an embodiment of the present invention. Referring to FIG. 6 and FIG. 4, a portable display 112 may be a virtual reality (VR) display or an augmented reality (AR) display. The image displayed by the portable display 112 is shown in FIG. 6. In FIG. 6, the user wears the portable display 112 and the image shows that the concentration of *Escherichia coli* BA in the ward is 1900 colony forming units/cubic meter (CFU/$m^3$).

Referring to FIG. 1, FIG. 2, and FIG. 4, the system 1 for notifying environmental pollution status may further include at least one wireless base station 12 and a cloud server 13. The wireless base station 12 may be, but not limited to, a 3G base station, a 4G base station, a 5G base station, a Bluetooth® base station, or a WiFi base station. For convenience and clarity, the number of the wireless base station 12 is one. The wireless base station 12 is wirelessly connected to the first wireless communication modules 104 of the wireless environment sensing devices 10 and the second wireless communication module 110 of the portable wireless environmental pollution status notification device 11. The cloud server 13 is electrically connected to the wireless base station 12. The wireless environment sensing devices 10 transmit the pollution related information P and the sensing locations S corresponding thereto to the cloud server 13 through the wireless base station 12. The cloud server 13 transmits the pollution related information P and the sensing locations S corresponding thereto to the portable wireless environmental pollution status notification device 11 through the wireless base station 12.

Specifically, the first processor 105 uses the first pollution parameter PO1 as pollution related information P and transmits the sensing location S and the first pollution parameter PO1 to the cloud server 12 through the first wireless communication module 104 and the wireless base station 12.

When the first pollution parameter PO1 is greater than a given value, the first processor 105 notifies the second processor 111 of the portable wireless environmental pollution status notification device 11 through the first wireless communication module 104, the wireless base station 12, and the cloud server 13 that the sensing location S corresponding to the first pollution parameter PO1 greater than the given value is a polluted location. When the first visible light image V1 has a human face image and the first temperature range is greater than a given temperature for a given time period, the first processor 105 notifies the second processor 111 of the portable wireless environmental pollution status notification device 11 through the first wireless communication module 104, the wireless base station 12, and the cloud server 13 that the sensing location S corresponding to the first temperature range greater than the given temperature is a polluted location. When the first visible light image V1 has a human face image and the first temperature range is greater than a given temperature for a given time period, the first processor 105 transmits the human face image to the second processor 111 of the portable wireless environmental pollution status notification device 11 through the first wireless communication module 104, the wireless base station 12, and the cloud server 13. When the first visible light image V1 has a human face image and the first pollution parameter PO1 is greater than a given value for a given time period, the first processor 105 transmits the human face image to the second processor 111 of the portable wireless environmental pollution status notification device 11 through the first wireless communication module 104, the wireless base station 12, and the cloud server 13.

In addition, the second processor 111 may receive reference signal received power (RSRP), signal-to-interference-plus-noise ratios (SINRs), packet round-trip time (RTT), angles of arrival, angles of departure, and the location of the wireless base station 12 from the wireless base station 12 through the second wireless communication module 110 and calculate the location of the second processor 111 as a starting location based on the RSRP, the SINRs, the packet RTT, the angles of arrival, the angles of departure, and the location of the wireless base station 12.

According to the embodiments provided above, the system for notifying environmental pollution status positioning uses wireless environment sensing devices to implement environmental detection distribution in three-dimensional space, thereby providing a recommended path.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. A system for notifying environmental pollution status comprising:

a plurality of wireless environment sensing devices respectively arranged in different sensing locations of a physical environment and configured to respectively store the sensing locations and respectively sense pollution related information corresponding to the different sensing locations to output the pollution related information and the sensing locations corresponding thereto; and a portable wireless environmental pollution status notification device wirelessly connected to the plurality of wireless environment sensing devices, located in the physical environment, and configured to receive the pollution related information and the sensing locations corresponding thereto and generate notification signals based on the pollution related information and the sensing locations corresponding thereto;

wherein each of the plurality of wireless environment sensing devices includes:

at least one first pollutant sensor configured to measure a first pollution parameter of first pollutants corresponding to the sensing location;

a first image sensor and a first thermal imaging camera configured to respectively capture a first visible light image and a first thermal image within the same range;

a storage device configured to store the sensing location;

a first wireless communication module wirelessly connected to the portable wireless environmental pollution status notification device; and a first processor electrically connected to the at least one first pollutant sensor, the first image sensor, the first thermal imaging camera, the storage device, and the first wireless communication module and configured to extract a first temperature range of the first thermal image, use the first pollution parameter as the pollution related information, and transmit the sensing location and the first pollution parameter to the portable wireless environmental pollution status notification device through the first wireless communication module;

wherein the notification signals include an image signal, a sound signal, and a vibration signal and the portable wireless environmental pollution status notification device includes:

a second wireless communication module wirelessly connected to the first wireless communication module;

a second processor electrically connected to the second wireless communication module and configured to receive the sensing location and the first pollution parameter through the second wireless communication module;

a portable display electrically connected to the second processor, wherein the second processor is configured to drive the portable display to generate the image signal based on a given condition, the sensing location, and the first pollution parameter;

at least one portable sound player electrically connected to the second processor, wherein the second processor is configured to drive the at least one portable sound player to generate the sound signal based on the sensing location and the first pollution parameter; and a portable vibrator electrically connected to the second processor, wherein the second processor is configured to drive the portable vibrator to generate the vibration signal based on the sensing location and the first pollution parameter;

wherein the given condition includes one of the different sensing locations as an ending location, the second processor is configured to receive reference signal received power (RSRP), signal-to-interference-plus-noise ratios (SINRs), packet round-trip time (RTT), angles of arrival, and angles of departure from the first wireless communication module through the second wireless communication module and calculate a starting location based on at least three of the different sensing locations and the RSRP, the SINRs, the packet RTT, the angles of arrival, and the angles of departure corresponding thereto, the second processor is configured to plan candidate paths connected between the ending location and the starting location based on the different sensing locations, calculate risk values corresponding to the candidate paths, and select the candidate path corresponding to a highest one or a lowest one of the risk values as a recommended path, $$\text{the risk value} = \sum_{i=1}^{n} \frac{Pi}{Di},$$

Di represents a distance between the starting location and a i-th the sensing location corresponding to the candidate path, Pi represents the first pollution parameter measured in a i-th the sensing location corresponding to the candidate path, n represents total number of the sensing locations corresponding to the candidate path, and the image signal shows the recommended path and an image corresponding to the sensing locations, the first pollutants, and the first pollution parameter.

2. The system for notifying environmental pollution status according to claim 1, wherein the plurality of wireless environment sensing devices are wirelessly connected to the portable wireless environmental pollution status notification device using WiFi direct technology and Bluetooth® technology.

3. The system for notifying environmental pollution status according to claim 1, wherein the first pollution parameter is a pollution concentration, a wind speed, a pollution range, or a flame burning intensity.

4. The system for notifying environmental pollution status according to claim 1, wherein when the first pollution parameter is greater than a given value, the first processor notifies the portable wireless environmental pollution status notification device through the first wireless communication module that the sensing location corresponding to the first pollution parameter greater than the given value is a polluted location.

5. The system for notifying environmental pollution status according to claim 1, wherein when the first visible light image has a human face image and the first temperature range is greater than a given temperature for a given time period, the first processor notifies the portable wireless environmental pollution status notification device through the first wireless communication module that the sensing location corresponding to the first temperature range greater than the given temperature is a polluted location.

6. The system for notifying environmental pollution status according to claim 1, wherein when the first visible light image has a human face image and the first temperature range is greater than a given temperature for a given time period, the first processor transmits the human face image to the portable wireless environmental pollution status notification device through the first wireless communication module.

7. The system for notifying environmental pollution status according to claim 1, wherein when the first visible light image has a human face image and the first pollution parameter is greater than a given value for a given time period, the first processor transmits the human face image to the portable wireless environmental pollution status notification device through the first wireless communication module.

8. The system for notifying environmental pollution status according to claim 1, wherein the at least one first pollutant sensor is an optical finger navigation (OFN) sensor.

9. The system for notifying environmental pollution status according to claim 1, wherein the first pollutants include bacteria, mold, viruses, flame, smoke, liquefied gas, carbon monoxide, carbon dioxide, ozone, alkane gases, benzene gases, ketone gases, natural gas, coal gas, gasoline, chlorine, ammonia, flammable gases, harmful volatile matter, or airborne matter.

10. The system for notifying environmental pollution status according to claim 1, wherein the at least one portable sound player includes a plurality of portable sound players.

11. The system for notifying environmental pollution status according to claim 1, wherein the portable wireless environmental pollution status notification device further includes:

at least one second pollutant sensor electrically connected to the second processor and configured to measure a second pollution parameter of second pollutants corresponding to the starting location, wherein the second pollutants and the first pollutants belong to identical pollutants and the second pollution parameter and the first pollution parameter belong to identical pollution parameters; and a second image sensor and a second thermal imaging camera electrically connected to the second processor and configured to respectively capture a second visible light image and a second thermal image within the same range corresponding to the starting location, the second processor is configured to obtain a second temperature range of the second thermal image, and when the sensing location is the starting location, the second processor respectively uses the second pollution parameter and the second temperature range to replace a corresponding the first pollution parameter and a corresponding the first temperature range.

12. The system for notifying environmental pollution status according to claim 11, wherein when the second pollution parameter is greater than a given value, the second processor drives the portable display to display that the sensing location corresponding to the second pollution parameter greater than the given value is a polluted location.

13. The system for notifying environmental pollution status according to claim 11, wherein when the second visible light image has a human face image and the second temperature range is greater than a given temperature for a given time period, the second processor drives the portable display to display the sensing position corresponding to the second temperature greater than the given temperature is a polluted location.

14. The system for notifying environmental pollution status according to claim 11, wherein when the second visible light image has a human face image and the second temperature range is greater than a given temperature, the second processor drives the portable display to display the human face image as a source of infection.

15. The system for notifying environmental pollution status according to claim 11, wherein when the second visible light image has a human face image and the second pollution parameter is greater than a given value for a given time period, the second processor drives the portable display to display the human face image as a source of infection.

16. A system for notifying environmental pollution status comprising:

a plurality of wireless environment sensing devices respectively arranged in different sensing locations of a physical environment and configured to respectively store the sensing locations and respectively sense pollution related information corresponding to the different sensing locations to output the pollution related information and the sensing locations corresponding thereto;

a portable wireless environmental pollution status notification device wirelessly connected to the plurality of wireless environment sensing devices, located in the physical environment, and configured to receive the pollution related information and the sensing locations corresponding thereto and generate notification signals based on the pollution related information and the sensing locations corresponding thereto;

at least one wireless base station wirelessly connected to the plurality of wireless environment sensing devices and the portable wireless environmental pollution status notification device; and a cloud server electrically connected to the at least one wireless base station, wherein the plurality of wireless environment sensing devices are configured to transmit the pollution related information and the sensing locations corresponding thereto to the cloud server through the at least one wireless base station, and the cloud server is configured to transmit the pollution related information and the sensing locations corresponding thereto to the portable wireless environmental pollution status notification device through the at least one wireless base station;

wherein each of the plurality of wireless environment sensing devices includes:

at least one first pollutant sensor configured to measure a first pollution parameter of first pollutants corresponding to the sensing location;

a first image sensor and a first thermal imaging camera configured to respectively capture a first visible light image and a first thermal image within the same range;

a storage device configured to store the sensing location;

a first wireless communication module wirelessly connected to the at least one wireless base station; and a first processor electrically connected to the at least one first pollutant sensor, the first image sensor, the first thermal imaging camera, the storage device, and the first wireless communication module and configured to extract a first temperature range of the first thermal image, use the first pollution parameter as the pollution related information, and transmit the sensing location and the first pollution parameter to the cloud server through the first wireless communication module and the at least one wireless base station;

wherein the notification signals include an image signal, a sound signal, and a vibration signal and the portable wireless environmental pollution status notification device includes:

a second wireless communication module wirelessly connected to the at least one wireless base station;

a second processor electrically connected to the second wireless communication module and configured to receive the sensing location and the first pollution parameter through the second wireless communication module;

a portable display electrically connected to the second processor, wherein the second processor is configured to drive the portable display to generate the image signal based on a given condition, the sensing location, and the first pollution parameter;

at least one portable sound player electrically connected to the second processor, wherein the second processor is configured to drive the at least one portable sound player to generate the sound signal based on the sensing location and the first pollution parameter; and a portable vibrator electrically connected to the second processor, wherein the second processor is configured to drive the portable vibrator to generate the vibration signal based on the sensing location and the first pollution parameter;

wherein the given condition includes one of the different sensing locations as an ending location, the second processor is configured to receive reference signal received power (RSRP), signal-to-interference-plus-noise ratios (SINRs), packet round-trip time (RTT), angles of arrival, angles of departure, and a location of the at least one wireless base station from the at least one wireless base station through the second wireless communication module and calculate a starting location based on the RSRP, the SINRs, the packet RTT, the angles of arrival, the angles of departure, and the location of the at least one wireless base station, the second processor is configured to plan candidate paths connected between the ending location and the starting location based on the different sensing locations, calculate risk values corresponding to the candidate paths, and select the candidate path corresponding to a highest one or a lowest one of the risk values as a recommended path, $$\text{the risk value} = \sum_{i=1}^{n} \frac{Pi}{Di},$$

Di represents a distance between the starting location and a i-th the sensing location corresponding to the candidate path, Pi represents the first pollution parameter measured in a i-th the sensing location corresponding to the candidate path, n represents total number of the sensing locations corresponding to the candidate path, and the image signal shows the recommended path and an image corresponding to the sensing locations, the first pollutants, and the first pollution parameter.

17. The system for notifying environmental pollution status according to claim 16, wherein the at least one wireless base station is a 3G base station, a 4G base station, a 5G base station, a Bluetooth® base station, or a WiFi base station.

18. The system for notifying environmental pollution status according to claim 16, wherein the first pollution parameter is a pollution concentration, a wind speed, a pollution range, or a flame burning intensity.

19. The system for notifying environmental pollution status according to claim 16, wherein when the first pollution parameter is greater than a given value, the first processor notifies the portable wireless environmental pollution status notification device through the first wireless communication module, the at least one wireless base station, and the cloud server that the sensing location corresponding to the first pollution parameter greater than the given value is a polluted location.

20. The system for notifying environmental pollution status according to claim 16, wherein when the first visible light image has a human face image and the first temperature range is greater than a given temperature for a given time period, the first processor notifies the portable wireless environmental pollution status notification device through the first wireless communication module, the at least one wireless base station, and the cloud server that the sensing location corresponding to the first temperature range greater than the given temperature is a polluted location.

21. The system for notifying environmental pollution status according to claim 16, wherein when the first visible light image has a human face image and the first temperature range is greater than a given temperature for a given time period, the first processor transmits the human face image to the portable wireless environmental pollution status notification device through the first wireless communication module, the at least one wireless base station, and the cloud server.

22. The system for notifying environmental pollution status according to claim 16, wherein when the first visible light image has a human face image and the first pollution parameter is greater than a given value for a given time period, the first processor transmits the human face image to the portable wireless environmental pollution status notification device through the first wireless communication module, the at least one wireless base station, and the cloud server.

23. The system for notifying environmental pollution status according to claim 16, wherein the at least one first pollutant sensor is an optical finger navigation (OFN) sensor.

24. The system for notifying environmental pollution status according to claim 16, wherein the first pollutants include bacteria, mold, viruses, flame, smoke, liquefied gas, carbon monoxide, carbon dioxide, ozone, alkane gases, benzene gases, ketone gases, natural gas, coal gas, gasoline, chlorine, ammonia, flammable gases, harmful volatile matter, or airborne matter.

25. The system for notifying environmental pollution status according to claim 16, wherein the at least one portable sound player includes a plurality of portable sound players.

26. The system for notifying environmental pollution status according to claim 16, wherein the portable wireless environmental pollution status notification device further includes:

at least one second pollutant sensor electrically connected to the second processor and configured to measure a second pollution parameter of second pollutants corresponding to the starting location, wherein the second pollutants and the first pollutants belong to identical pollutants and the second pollution parameter and the first pollution parameter belong to identical pollution parameters; and a second image sensor and a second thermal imaging camera electrically connected to the second processor and configured to respectively capture a second visible light image and a second thermal image within the same range corresponding to the starting location, the second processor is configured to obtain a second temperature range of the second thermal image, and when the sensing location is the starting location, the second processor respectively uses the second pollution parameter and the second temperature range to replace a corresponding the first pollution parameter and a corresponding the first temperature range.

27. The system for notifying environmental pollution status according to claim 16, wherein when the second pollution parameter is greater than a given value, the second processor drives the portable display to display that the sensing location corresponding to the second pollution parameter greater than the given value is a polluted location.

28. The system for notifying environmental pollution status according to claim 16, wherein when the second visible light image has a human face image and the second temperature range is greater than a given temperature for a given time period, the second processor drives the portable display to display the sensing position corresponding to the second temperature greater than the given temperature is a polluted location.

29. The system for notifying environmental pollution status according to claim 16, wherein when the second visible light image has a human face image and the second temperature range is greater than a given temperature, the second processor drives the portable display to display the human face image as a source of infection.

30. The system for notifying environmental pollution status according to claim 16, wherein when the second visible light image has a human face image and the second pollution parameter is greater than a given value for a given time period, the second processor drives the portable display to display the human face image as a source of infection.

* * * * *